(12) United States Patent
Voskuilen et al.

(10) Patent No.: US 12,734,058 B2
(45) Date of Patent: Sep. 15, 2026

(54) ANKLE SUPPORT COMPRISING AN ONE-PIECE SHELL HAVING A LATERAL SHELL SECTION, AND A MEDIAL SHELL SECTION

(71) Applicant: NEA INTERNATIONAL B.V., Maastricht-Airport (NL)

(72) Inventors: Agnes Theodora Maria Voskuilen, Maastricht-Airport (NL); Jeroen Hendrik Johan Koeslag, Maastricht-Airport (NL)

(73) Assignee: NEA INTERNATIONAL B.V., Maastricht-Airport (NL)

( * ) Notice: Subject to any disclaimer, the term of this patent is extended or adjusted under 35 U.S.C. 154(b) by 152 days.

(21) Appl. No.: 18/714,994

(22) PCT Filed: Dec. 7, 2022

(86) PCT No.: PCT/NL2022/050705

§ 371 (c)(1),
(2) Date: May 30, 2024

(87) PCT Pub. No.: WO2023/121437

PCT Pub. Date: Jun. 29, 2023

(65) Prior Publication Data

US 2025/0025324 A1 Jan. 23, 2025

(30) Foreign Application Priority Data

Dec. 20, 2021 (NL) ..................................... 2030191

(51) Int. Cl.
*A61F 5/01* (2006.01)

(52) U.S. Cl.
CPC .................................. *A61F 5/0111* (2013.01)

(58) Field of Classification Search
CPC .... A61F 5/0111; A61F 5/0113; A61F 5/0127; A61F 5/0585; A61F 5/14
See application file for complete search history.

(56) References Cited

U.S. PATENT DOCUMENTS 5,219,324 A 6/1993 Hall
6,245,035 B1 * 6/2001 Schrijver .............. A61F 5/0111 602/65

(Continued)

FOREIGN PATENT DOCUMENTS

WO 9829060 A1 7/1998
WO 2018056812 A1 3/2018

OTHER PUBLICATIONS

European Patent Office, International Search Report received in International Application No. PCT/NL2022/050705, Jan. 5, 2023, 2 pages.

*Primary Examiner* — Kari K Rodriquez
(74) *Attorney, Agent, or Firm* — Suiter Swantz IP

(57) ABSTRACT

The invention relates to an ankle support comprising an one-piece shell having:
- a lateral shell section,
- a medial shell section which has an elongated reinforced zone for providing support in the ankle support such that by means of the elongated reinforced zone the lateral shell section is substantially less stiffer than the medial shell section, and
- a sole shell section connecting the lateral shell section and the medial shell section, wherein the medial shell section comprises a medial edge configured to run upwards from the sole shell section along the medial side of lower leg and defining an open recess in the medial shell section for the medial malleolus.

19 Claims, 6 Drawing Sheets

(56) References Cited

U.S. PATENT DOCUMENTS

| | | | | |
|---|---|---|---|---|
| 6,929,617 | B2 * | 8/2005 | McCormick | A61F 5/0111<br>602/65 |
| 7,785,283 | B1 * | 8/2010 | Bledsoe | A61F 5/0102<br>602/29 |
| 8,641,654 | B2 * | 2/2014 | Verkade | A61F 5/0111<br>602/65 |
| 9,421,117 | B1 * | 8/2016 | Hames | A61F 5/0111 |
| 11,103,376 | B1 * | 8/2021 | Gramaglia | A61F 5/0127 |
| 11,344,442 | B1 * | 5/2022 | McVeigh | A61F 5/0111 |
| 2004/0236259 | A1 | 11/2004 | Pressman et al. | |
| 2010/0106066 | A1 * | 4/2010 | Hess | A61F 5/0111<br>602/27 |
| 2017/0165094 | A1 * | 6/2017 | Voskuilen | A61F 5/0111 |

* cited by examiner

ANKLE SUPPORT COMPRISING AN ONE-PIECE SHELL HAVING A LATERAL SHELL SECTION, AND A MEDIAL SHELL SECTION

TECHNICAL FIELD AND BACKGROUND

The invention relates to an ankle support comprising an one-piece shell having a lateral shell section, and a medial shell section.

The invention also relates to a method for producing an ankle support.

Such an ankle support comprising an one-piece shell is for example known from WO98/29060. This known ankle support comprises a lateral shell section and a medial section, wherein this two shell sections have an asymmetrical configuration. This ankle support provides stability against the tendency of the foot of twisting inwards and allows most normal foot movements without irritation. It is an object of the present invention to provide an ankle support which provides maximum comfort for a user, a stable medial shell section which prevents a foot of twisting inwards and a lateral shell section providing maximum freedom of movement.

BRIEF SUMMARY OF THE INVENTION

This object is achieved by an ankle support according to claim 1.

The ankle support comprising an one-piece shell has:

- a lateral shell section,
- a medial shell section which is larger than the lateral shell section and which has an elongated reinforced zone for providing support in the ankle support such that by means of the elongated reinforced zone the lateral shell section is substantially less stiffer than the medial shell section, and
- a sole shell section connecting the lateral shell section and the medial shell section, wherein the medial shell section comprises a medial edge configured to run upwards from the sole shell section along the medial side of lower leg and defining an open recess in the medial shell section for the medial malleolus, and the lateral shell section comprises a lateral edge configured to run upwards from the sole shell section along the lateral side of the lower leg and defining an open recess in the lateral shell section for the lateral malleolus.

The medial shell section of the ankle support is configured to provide maximum stability and maximum comfort such that a user is able to receive the desired support of the ankle support for a full day without irritation. Further, maximum freedom of movement without impeding the normal gait cycle is provided by means of the relatively small dimensioned lateral shell section during use of the ankle support on a foot and lower leg of a user. The ankle support provides a more optimal support for an unstable ankle. For example, the ankle support is used in the treatment of subacute lateral ankle ligament injury at the moment that the respective ankle can be loaded again. The lateral shell section has been dimensioned in such a manner that this lateral shell section comprises a lateral edge configured to run upwards from the sole shell section along the lateral side of the lower leg and defining an open recess in the lateral shell section for the lateral malleolus. In other words, if the ankle support is worn by a user, the lateral edge of the lateral shell section runs from a position which lies below the lateral malleolus, upwards along the lateral malleolus and then further upwards along a part of the lower leg above lateral malleolus. The lateral shell section has a smaller horizontal distance measured between the lateral edge and the heel or back of the leg in the recess than a parallel horizontal distance measured between the lateral edge and the heel or back of the leg above or below the recess. As a result of the open recess in the lateral shell section for the lateral malleolus, the ankle support provides maximum freedom of movement.

The ankle support further comprises an elastic cover which is more elastic than the lateral shell section, for example because the elastic cover is made from a different material than the shell. In the ankle support at least a portion of the lateral edge is connected to the elastic cover, wherein a portion of the elastic cover opposite to the lateral edge is configured to be releasably connected to an upper portion of the medial shell section. In use of the ankle support, the elastic cover connected to the lateral edge of the lateral shell section is applied over the front portion of the leg and/or the foot instep and attached in a releasable manner to the upper portion of the medial shell section. The elastic cover attached to the upper portion of the medial shell section results in an ankle support which makes it impossible or almost impossible that a foot of a user will twist inwards during use. The elastic cover is or resembles an elastic bandage, i.e. a stretchable bandage used to create local pressure and/or compression, such that the elastic cover applies in use a stable and user-friendly pressure. This pressure may be for example used to treat inversion traumas and/or to restrict swelling of the ankle. In one aspect, the lateral edge may be largely connected to the elastic cover, for example more than 50% or even more preferred more than 75%, such that in use the elastic cover may cover a relatively large portion of the front leg and/or the foot instep compared to straps used for fixing the ankle support to the lower leg and foot of a user. In a further aspect, the elastic cover comprises a strap section or strap sections and a textile section, wherein the textile section of the elastic cover is more elastic than the strap section of the elastic cover. The main function of the textile section is providing the above described local pressure and/or compression, wherein the strap section serves a strong and reliable fixation of the ankle support on a foot and a lower leg of a user. In addition, at least one strap section prevents in use of the ankle support that a foot of a user will twist inwards during use. Further, the textile section may be made of a breathable fabric. Advantageously, the strap section may be made of at least two stacked layers, wherein a first layer of the at least two stacked layers is less elastic than the textile section, for example the first layer is made of plastics such as a thermoplastic elastomer, wherein the first layer is connected on a second layer formed by the textile section to provide the strap section made of at least two stacked layers. A first edge area of the elastic cover extending between the sole section and the portion of the elastic cover to be releasably connected to the upper portion of the medial shell section may be provided by the strap section. The textile section may be made from a double folded textile to provide a strong and long lasting textile section. An edge of the elastic cover between the portion to be releasably connected to the upper portion of the medial shell section and the lateral edge may be provided by a fold line of the double folded textile of the textile section. This edge provides comfort to a user wearing the ankle support and in addition provides an edge with a relatively long lifespan, because the risk of fraying of this textile upper is reduced significantly. The lifespan may be further extended when a second edge area of the elastic cover connected to the lateral edge of the lateral shell section is formed by the strap section.

In one other aspect, the ankle support further may comprise at least one strap comprising two strap portions and each strap portion is connected to the sole shell section. One of these two strap portions is connected close to the sole shell section to the lateral shell section and the other of the two strap portions is connected close to the sole shell section to the medial shell section. Alternatively, the ankle support may comprise two separate straps and each strap is connected to the sole shell section, wherein one of the two straps is connected close to the sole shell section to the lateral shell section and the other of the two straps is connected close to the sole shell section to the medial shell section. The strap portions or the straps are not only connected to the sole section, but also to the medial shell section and the lateral shell section. By means of the connection to the medial shell section and the lateral shell section, the strap portions or the straps always extend at an angle larger than 90 degrees and smaller than 180 degrees with respect to the sole section, wherein the angle normally lies between 120-160 degrees. Such an angle facilitates the instep for a user into the ankle support to be attached to the user's foot and lower leg. The angle on both sides of the sole section may vary, such that it is possible to use the angle difference to provide an indication to the user of the sequence which of the two strap portions or straps should be attached before the other. The strap portion or strap having the smallest angle with respect to the sole section will in an inactive (unconnected) condition extend to a higher position seen from the sole section than the other strap portion or strap, such that a perceptible indication for a user can be provided of the order of attaching the strap portions or straps around the foot and the lower leg of the user. This strap sequence indicator provides a more user-friendly ankle support and reduces the risk that the straps are attached in an incorrect manner.

Each transition area of the one-piece shell of the ankle support between the lateral/medial shell section and the sole shell section is provided with at least one notch for guiding the strap or strap portion to the lateral/medial shell section such that a part of the strap or strap portion can be connected to the lateral/medial shell section. These notches facilitate a smooth course of the strap or strap portion connected to the lateral/medial shell section to reduce the risk that the straps or strap portions wrinkle and/or fold in an uncomfortable way to guarantee no irritation for a user wearing the ankle support.

In another aspect, the one-piece shell of the ankle support is made by multi-material injection molding for creating a single-structure part with different regional materials or different regional material properties, for example the elongated reinforced zone providing a relatively stiff medial shell section with respect to the lateral shell section. The reinforced zone of the medial shell section runs from or close to the sole shell section along the medial malleolus further upwards. By using multi-material injection molding, it is possible to produce a one-piece shell anatomically adapted to the contours of the ankle, foot and leg along which it runs such that the shell provides maximum freedom of movement in directions other than the directions to be stabilized by means of the one-piece shell. The basis material of the one-piece shell may be made of plastics, preferably thermoplastic elastomers, wherein at least the elongated reinforced zone may comprise glass fibres. Further, by using multi-material injection molding to produce the one-piece shell, it is possible to provide a semi-rigid frame which can be soft and comfortable for a user. The one-piece shell may have different layers, including for example at least an inner core layer, wherein the inner core layer may be configured to be less flexible than the material close to the edges of the one-piece shell for example by varying the thickness of the material used to produce the one-piece shell and by using different materials. An inner core layer can be made of fibre-reinforced plastic, wherein the surfaces of the one-piece shell in contact with the used can be made of another plastic material, such as a more soft and/or a skin-friendly plastic. By varying the thickness of the core layer in the support frame provided by the one-piece shell, it is possible to vary the rigidity in the support frame. For example, the core layer may have the greatest thickness in the elongated reinforced zone providing a relatively stiff medial shell section with respect to the lateral shell section. The one-piece shell of the ankle support may comprise a circumferential edge or circumferential edges which is more flexible than the elongated reinforced zone of the medial shell section in order to further increase the comfort of the ankle support for a user wearing the ankle support. Further, the circumferential edge or edges of the one-piece shell can be easily used for connecting, for example by stitching and/or bonding, other components of the ankle support such as for example the elastic cover discussed above.

The lateral shell section may comprise at least one zone which is stiffer than another zone of the lateral shell section, but less stiff than the elongated reinforced zone of the medial shell section, preferably the lateral shell section comprises an upper part, a middle part and a lower part connected to the sole section, wherein at least the upper part comprises a stiffened zone which makes the upper part stiffer than the middle part. In this way it is possible to provide a semi-rigid frame providing maximum comfort for a user and maximum stabilization by means of the medial shell section, in particular in combination with the above described elastic cover. The one-piece shell may be configured to leave the front part of the lower leg free such that the one-piece shell provides a semi-rigid frame defining a user-friendly open instep space for receiving a foot and a lower leg of a user. Further, the sole shell section may comprise a reinforced sole zone which extends between the medial and lateral shell sections, wherein the reinforced sole zone is stiffer than the lateral shell section and/or the reinforced zone of the medial shell section is stiffer than the reinforced sole zone.

The medial shell section and the lateral shell section may define a heel recess, preferably a heel recess having an endless heel recess edge, optionally in combination with the sole shell section. Above the heel recess the medial shell section and the lateral shell section merge into another.

It is further an object to provide a method for producing the above described ankle support which provides maximum comfort for a user, a stable medial shell section which prevents a foot of twisting inwards and a lateral shell section providing maximum freedom of movement. This object is achieved by providing an ankle support having a one-piece shell which is manufactured by multi-material injection molding.

BRIEF DESCRIPTION OF THE DRAWINGS

The present invention will be explained in more detail below with reference to the appended figures showing an exemplary embodiment of an ankle support.

DETAILED DESCRIPTION OF THE INVENTION

Figure 1:
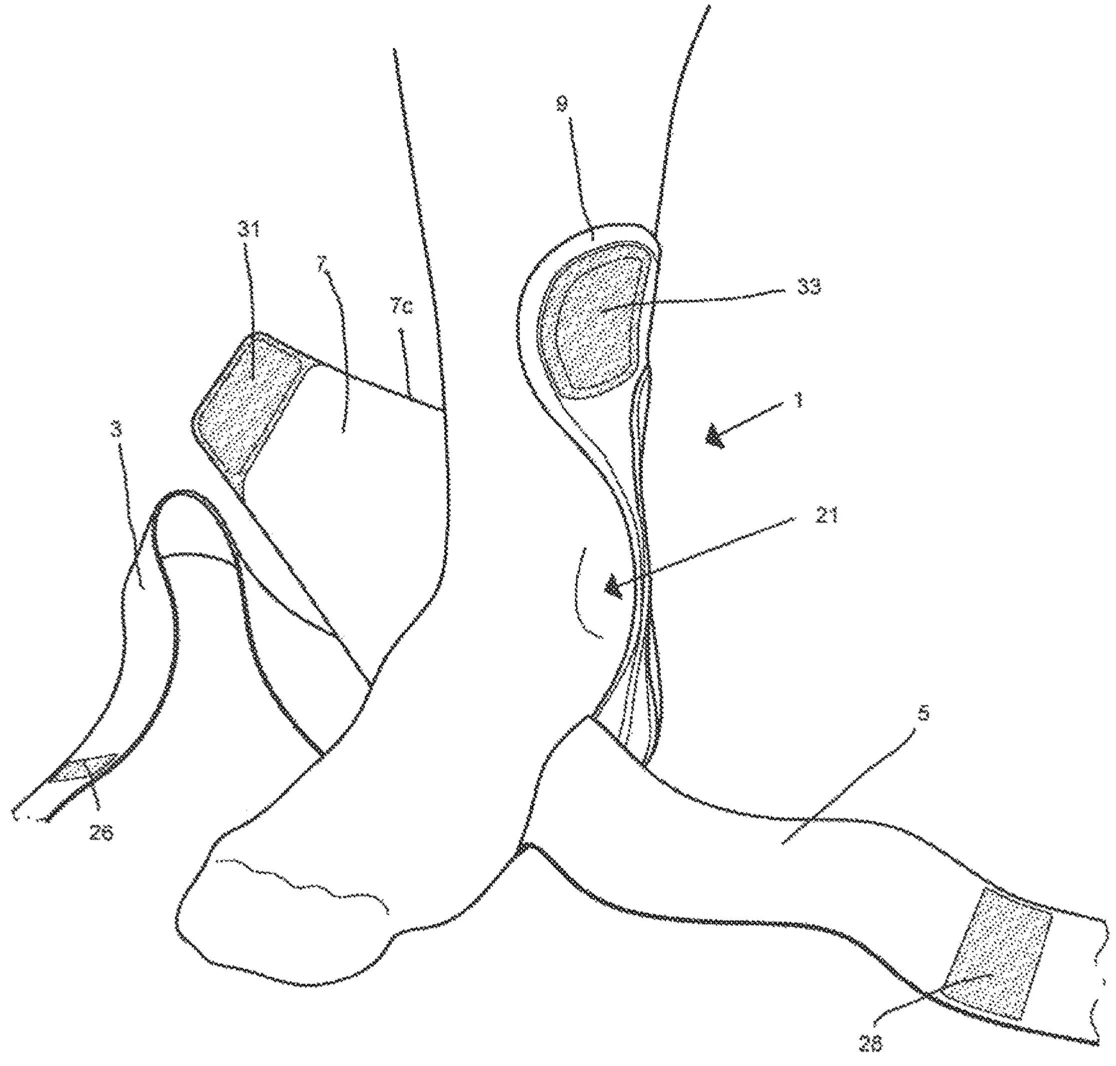
FIG. 1 shows a perspective view of an ankle support embodiment around a lower leg and foot of a user in a unfixed manner.

Like parts are indicated by the same reference signs in the various figures.

Each feature disclosed with reference to the figure can also be combined with another feature disclosed in this disclosure including the claims, unless it is evident for a person skilled in the art that these features are incompatible.

FIGS. 1-6 show various views of an exemplary embodiment of an ankle support 1.

The ankle support 1 comprises two straps or two strap portions 3, 5, an elastic cover 7 and a one-piece shell 9. The one-piece shell 9 comprises a lateral shell section 11 (FIG. 3), a medial shell section 13 (FIG. 4) which is larger than the lateral shell section 11 and which has an elongated reinforced zone 15 for providing support in the ankle support 1 such that by means of the elongated reinforced zone 15 the medial shell section 13 is substantially stiffer than the lateral shell section 11. The one-piece shell 9 further comprises a sole shell section 17 (FIG. 5) connecting the lateral shell section 11 and the medial shell section 13. The medial shell section 13 and the lateral shell section 11 are configured to provide a stable medial shell section 13 which prevents a foot of twisting inwards and a lateral shell section providing maximum freedom of movement. In this way it is possible to provide an ankle support 1 providing maximum comfort for a user. Hence, the medial shell section 13 provides a medial rigid reinforcement by means of the elongated reinforced zone 15. In addition, the medial shell section 13 comprises a medial edge 19 configured to run upwards from the sole shell section 15 along the medial side of lower leg and defining an open recess 19 in the medial shell section 13 for the medial malleolus 21. The lateral shell section 11 provides maximum freedom of movement, in that the lateral shell section 11 comprises a lateral edge 23 configured to run upwards from the sole shell section 15 along the lateral side of the lower leg and defining an open recess 25 in the lateral shell section 11 for the lateral malleolus (not shown).

The ankle support 1 further comprises the elastic cover 7 which is more elastic than the lateral shell section 11. In the ankle support 1 shown in the figures the lateral edge is largely connected to the elastic cover 7. A portion 31 of the elastic cover 7 opposite to the lateral edge is configured to be releasably connected to an upper portion 33 of the medial shell section 13. As shown in FIG. 1, the elastic cover 7 connected to the lateral edge 23 of the lateral shell section 11 can be applied over the front portion of the leg and/or the foot instep and attached in a releasable manner to the upper portion 33 of the medial shell section 15. The elastic cover 7 is an elastic bandage, i.e. a stretchable bandage used to create local pressure and/or compression, such that the elastic cover applies in use a stable and user-friendly pressure.

Figure 3:
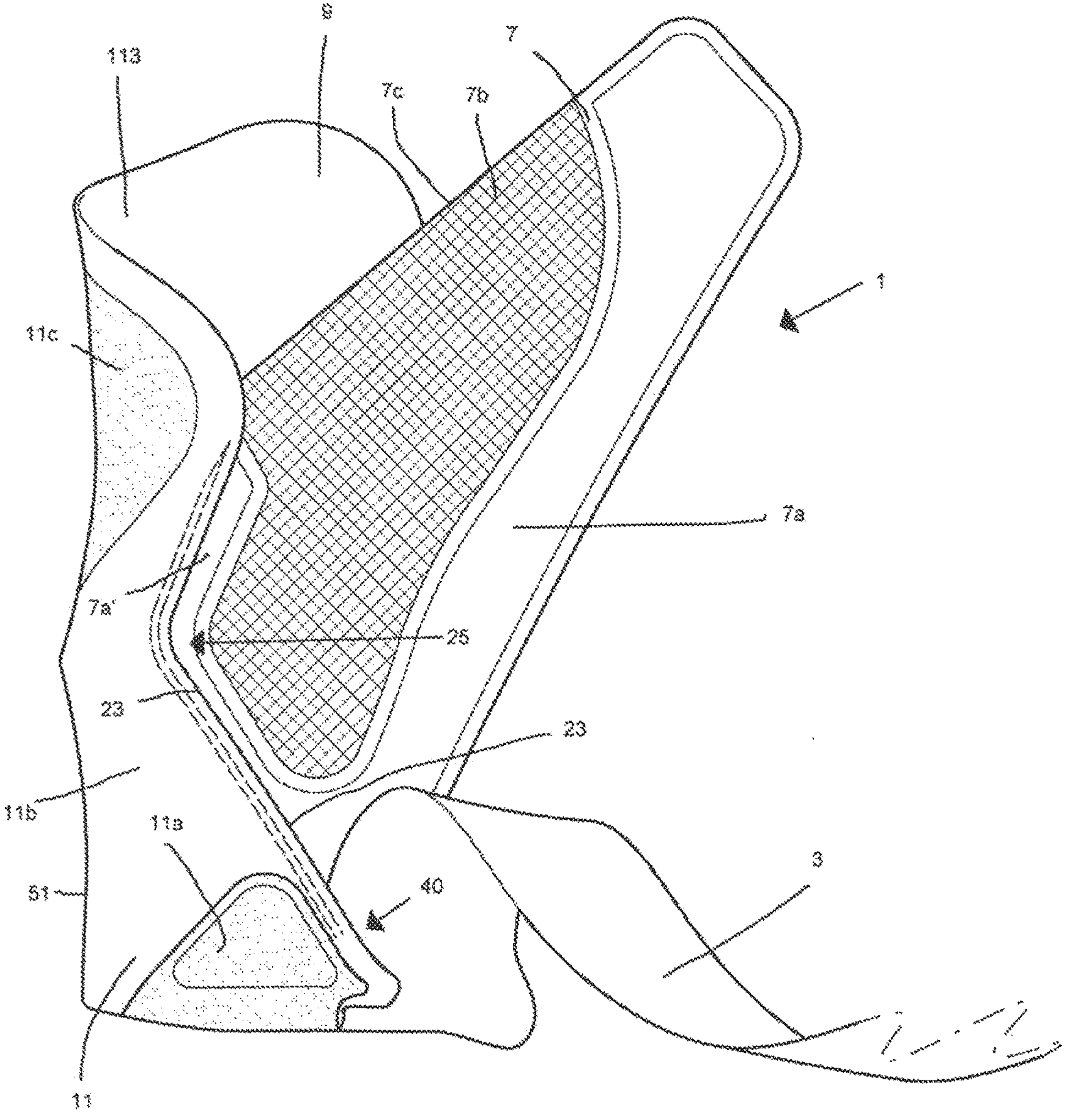
FIG. 3 shows a side view of the ankle support embodiment shown in FIG. 1 showing details of the lateral side of the ankle support.

The elastic cover 7 has a relatively wide side connected for example by stitching (dotted lines close to edge 23 in FIG. 3) to the lateral shell section 11 and an opposite side of the elastic cover to be attached in a releasable manner to the upper portion 33 of the medial shell section 13 has a relatively small width, i.e. a smaller width than the relative wide side connected the lateral shell section 11. As a result of its relatively large dimension, the elastic cover 7 is able to cover a relatively large portion of the front leg and/or the foot instep compared for example to the straps 3, 5 which are also used for fixing the ankle support to the lower leg and foot of a user. As shown in FIG. 3, the elastic cover 7 comprises a strap section 7*a* or strap sections 7*a*, 7*a*' and a textile section 7*b*, wherein the textile section 7*b* of the elastic cover 7 is more elastic than the strap sections 7*a*, 7*a*' of the elastic cover. In the embodiment shown in the figures sections 7*a*, 7*a*' merge into each other as shown in FIG. 3. The main function of the textile section 7*b* is providing improved local pressure and/or compression, wherein strap section 7*a*, 7*a*' serves a strong and reliable fixation of the ankle support 1 on a foot and a lower leg of a user. The strap section 7*a*, 7*a*' is made of at least two stacked layers, wherein a first layer of the at least two stacked layers is less elastic than the textile section. The first layer is connected on top of a second layer which is formed by the textile section to provide the strap section 7*a*, 7*a*'. A first edge area of the elastic cover indicated in FIG. 3 by strap section 7*a* extending between the sole section 17 and the portion 31 of the elastic cover 7 to be releasably connected to the upper portion 33 of the medial shell section 13 is provided by the strap section 7*a*. The textile section 7*b* is made from a double folded textile to provide a strong and long lasting textile section. An edge 7*c* of the elastic cover 7 between the portion 31 to be releasably connected to the upper portion 33 of the medial shell section 13 and the lateral edge 23 is provided by a fold line of the double folded textile of the textile section 7*b*. This edge 7*c* provides comfort to a user wearing the ankle support and in addition provides an edge 7*c* with a relatively long lifespan, because the risk of fraying of this textile edge is reduced significantly. The lifespan is further extended when the area of the elastic cover 7 connected to the lateral edge 23 of the lateral shell section 11 is formed by the strap section 7*a*' as shown in FIG. 3.

Figure 2:
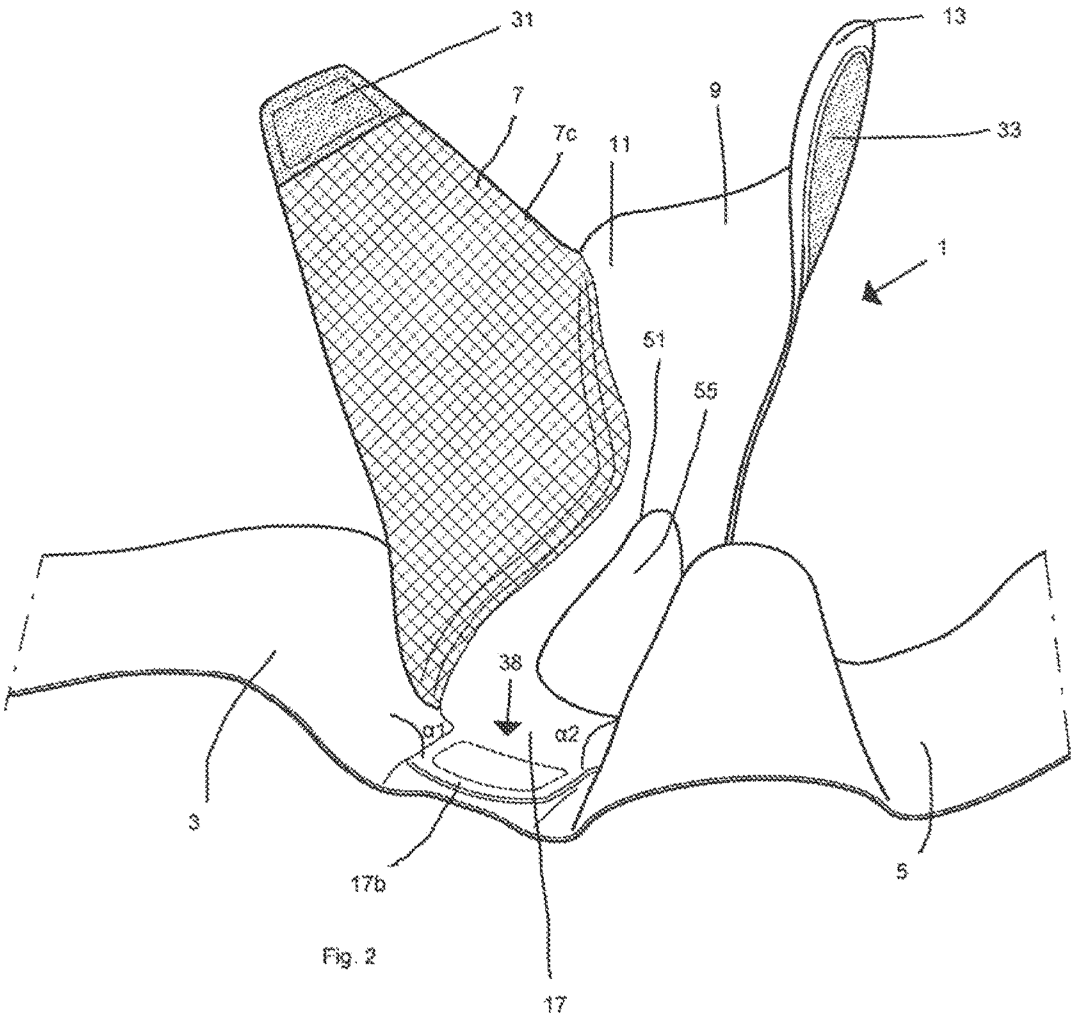
FIG. 2 shows perspective view of the ankle support embodiment shown in FIG. 1 not being worn by a user.

The ankle support 1 comprises one strap comprising two strap portions 3, 5 and each strap portion 3, 5 is connected to the sole shell section 17 indicate by arrow 38 in FIG. 2. One of these two strap portions 3 is connected close to the sole shell section 17 to the lateral shell section 11 indicated by arrow 40 in FIG. 3 and the other of the two strap portions 5 is connected close to the sole shell section 17 to the medial shell section 13 indicated by arrow 42. Alternatively, the ankle support may comprise two separate straps (not shown) instead of one strap with strap portions, wherein the two straps are connected in a similar manner as the strap portions 3, 5 shown in the figures. By connecting the strap portions 3, 5 to the sole section 17 and the medial shell section 13 and the lateral shell section 11, the strap portions 3, 5 always extend at an angle $\alpha 1$, $\alpha 2$ (FIG. 2) which is larger than 90 degrees and smaller than 180 degrees with respect to the sole section 17, wherein the angle $\alpha 1$, $\alpha 2$ normally lies between 120-160 degrees. Such an angle facilitates the instep for a user into the ankle support 1 to be attached to the user's foot and lower leg. The angle on both sides of the sole section varies, such that it is possible to use the angle difference to provide an indication to the user of the sequence which of the two strap portions 3, 5 or straps should be attached before the other. The strap portion 5 having the smallest angle $\alpha 2$ with respect to the sole section 17 will in an inactive (unconnected) condition extend to a higher position seen from the sole section 17 than the other strap portion 3, such that a perceptible indication for a user can be provided of the order of attaching the strap portions 3, 5 around the foot and the lower leg of the user. Each strap portion 3, 5 is provided with fasteners 26, 28, 58, for example by means of hook and loop fasteners, for fixing the strap portions 3, 5 at predetermined positions around the foot and the lower leg of the user.

Figure 5:
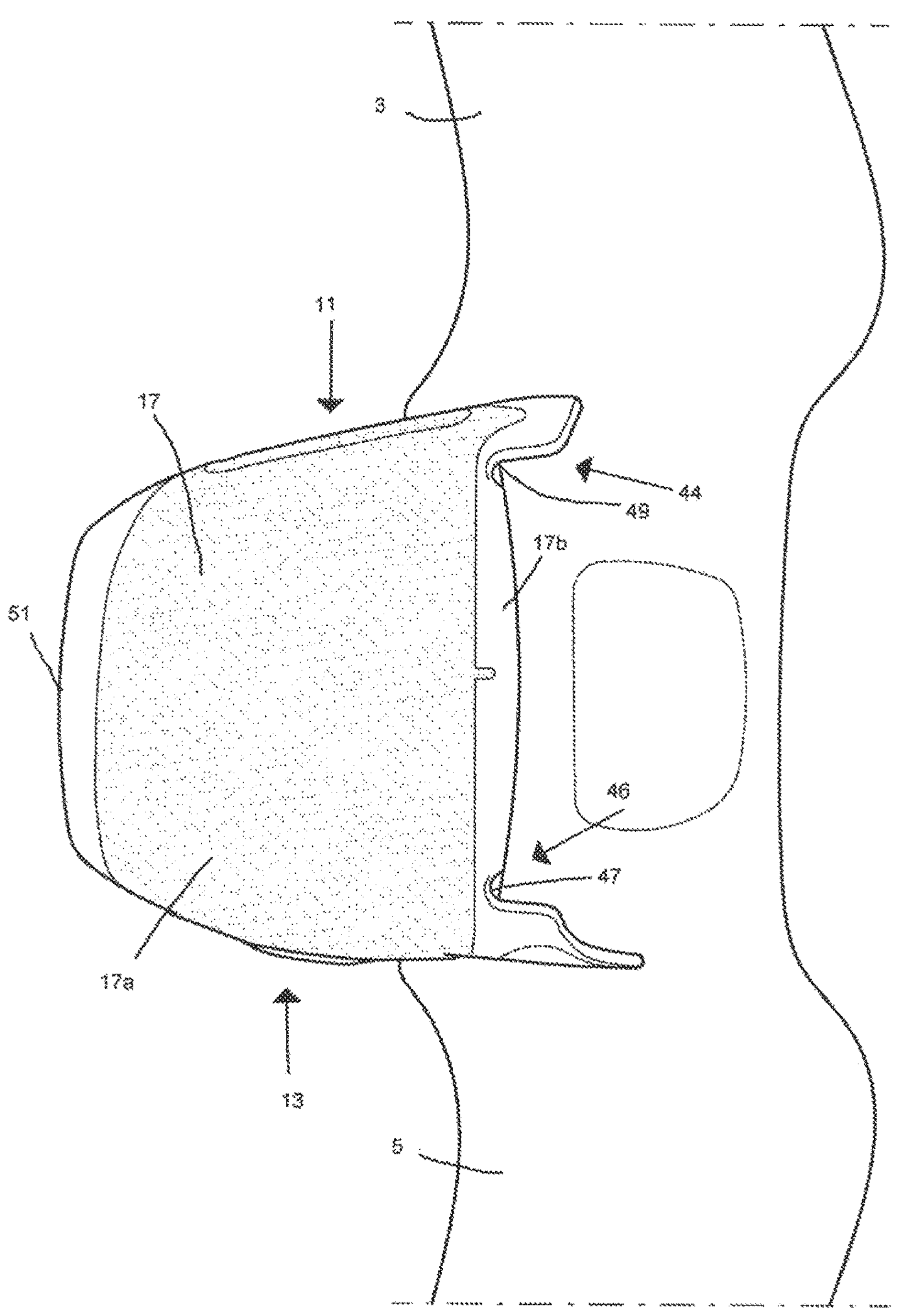
FIG. 5 shows a bottom view of the ankle support embodiment shown in FIG. 1 showing details of the bottom side of the ankle support.
Figure 6:
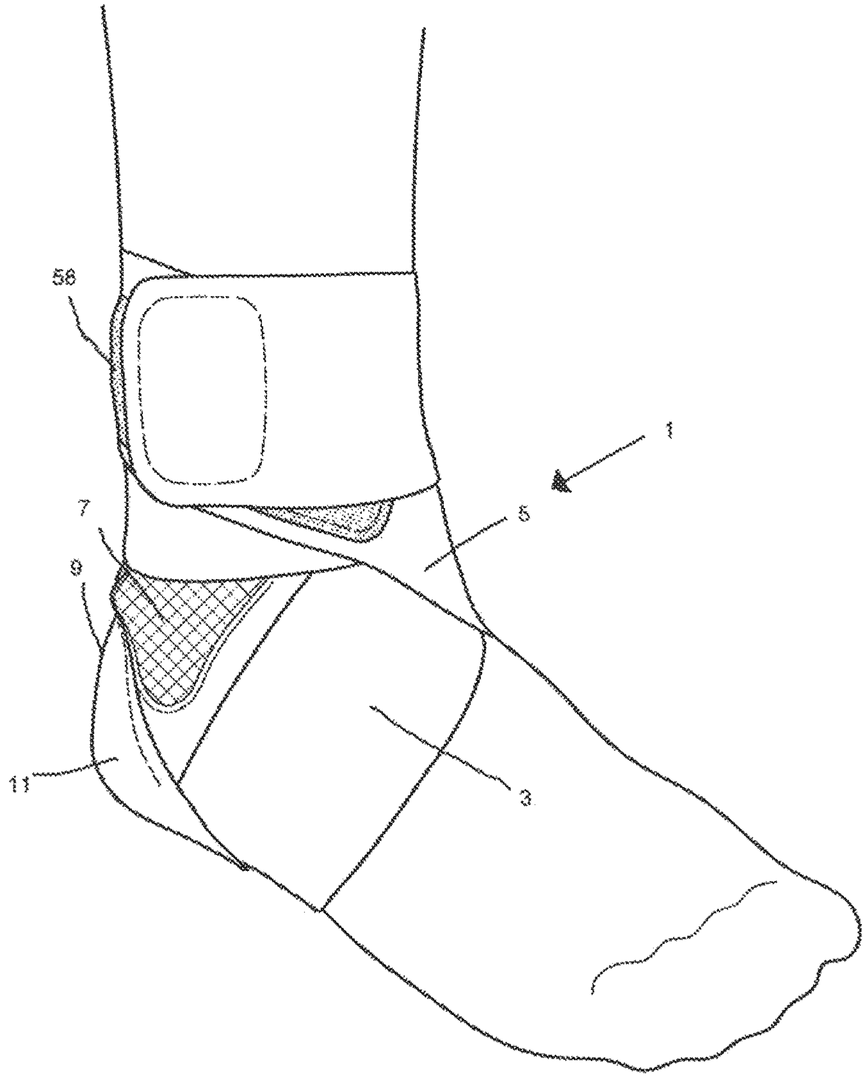
FIG. 6 shows a perspective view of the ankle support embodiment shown in FIG. 1 around a lower leg and foot of a user in a fixed manner.

With reference to FIG. 5, each transition area 44, 46 of the one-piece shell 9 of the ankle support 1 between the lateral 11/medial shell section 13 and the sole shell section 17 is provided with at least one notch 47, 49 for guiding the strap portion 3, 5 to the lateral 11/medial shell section 13 such that a part of each strap portion 3, 5 can be connected to the lateral/medial shell section. These notches 47, 49 facilitate a smooth course of the strap portions 3, 5 connected to the lateral/medial shell section to reduce the risk that the strap portions 3, 5 wrinkle and/or fold in an potentially uncomfortable way for a user wearing the ankle support 1.

Figure 4:
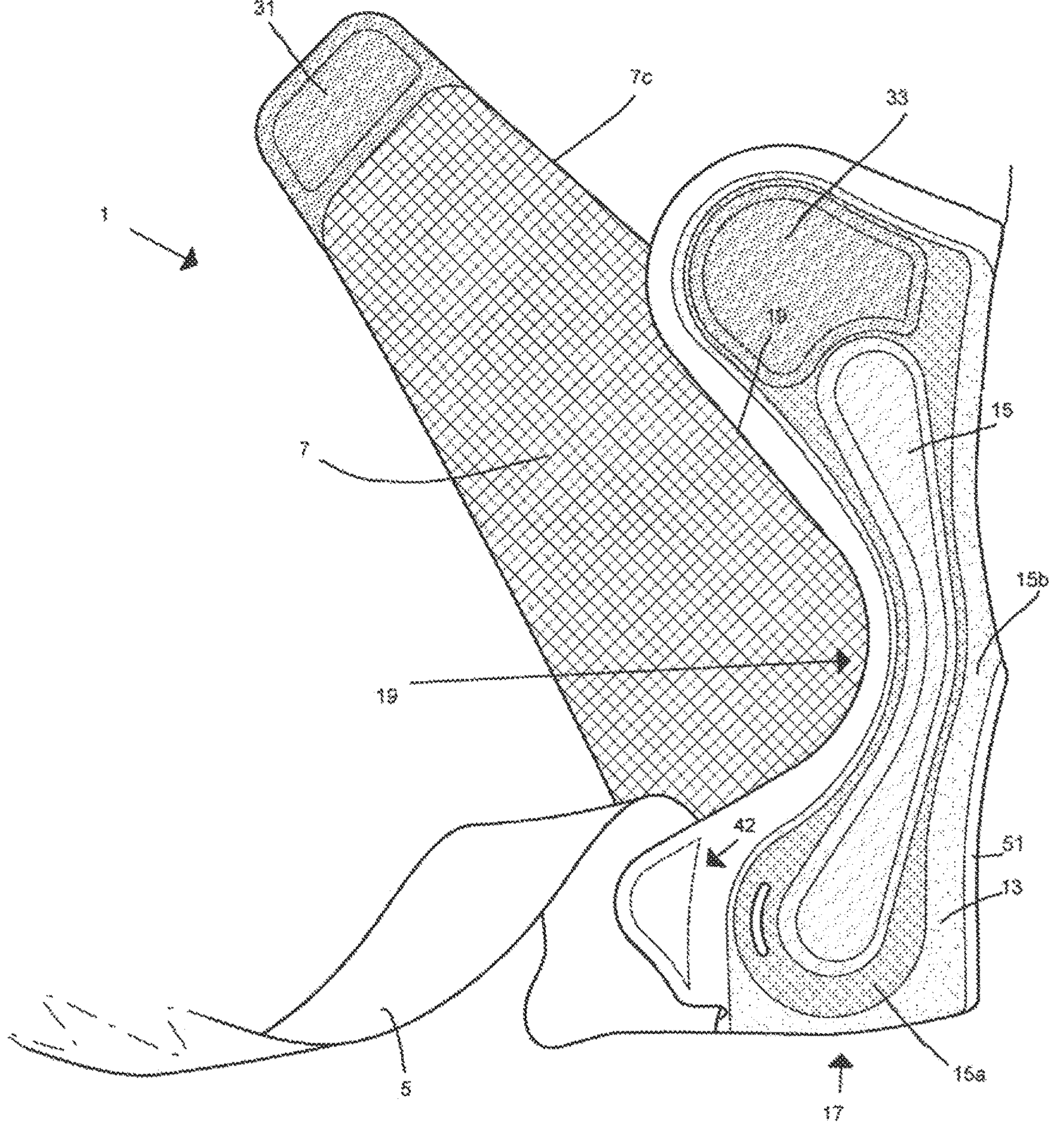
FIG. 4 shows a side view of the ankle support embodiment shown in FIG. 1 showing details of the medial side of the ankle support.

The one-piece shell 9 of the ankle support 1 is made by multi-material injection molding for creating a single-structure part with different regional materials or different regional material properties, for example the elongated reinforced zone 15 providing a relatively stiff medial shell section 13 with respect to the lateral shell section 11. The reinforced zone 15 of the medial shell section 13 runs from or close to the sole shell section 17 along the medial malleolus 21 further upwards. By using multi-material injection molding, it is possible to produce a one-piece shell 9 anatomically adapted to the contours of the ankle, foot and leg along which it runs such that the shell provides maximum freedom of movement in directions other than the directions to be stabilized by means of the one-piece shell. The basis material of the one-piece shell 9 is for example thermoplastic elastomers, wherein at least the elongated reinforced zone 15 comprises glass fibres or thermoplastic polyurethane glass fiber-reinforced. The one-piece shell may have different layers, including for example at least an inner core layer for example in the reinforced zone 15, wherein the inner core layer may be configured to be less flexible than the material close to the edges 19, 23, and heel recess edge 51 of the one-piece shell. By varying the thickness of the core layer or the one-piece shell 9 for example in combination with material properties or material compositions, it is possible to vary the rigidity in the one-piece shell 9. For example, the core layer or the one-piece shell may have the greatest thickness in the elongated reinforced zone 15 providing a relatively stiff medial shell section 13 with respect to the lateral shell section 11. As shown in FIG. 4, the medial shell section 13 may have various zones 15, 15*a*, 15*b*, wherein the zone 15 is stiffer (less flexible) than zone 15*a*, and zone 15*a* is stiffer (less flexible) than zone 15*b*. The one-piece shell of the ankle support may comprise circumferential edges 19, 23, 51 which are more flexible than the elongated reinforced zone 15 of the medial shell section 13 or even the zone 15*b* in order to further increase the comfort of the ankle support 1 for a user wearing the ankle support 1. Further, the circumferential edges 19, 23, 51 of the one-piece shell 9 can be easily used for connecting, for example by stitching (see dotted lines close to edge 23 in FIG. 3) and/or bonding, other components of the ankle support such as for example the elastic cover 7 as discussed above.

The lateral shell section 11 may comprise zones 11*a*, 11*b*, 11*c*, wherein zones 11*a*, 11*c* are stiffer than zone 11*b* of the lateral shell section 11, but less stiff than the elongated reinforced zone 15 of the medial shell section 13. The zone 11*c* is located in a upper part of the lateral shell section, zone 11*b* is mainly forming a middle part and a lower part connected to the sole section may comprise zone 11*a*. In this way it is possible to provide an ankle support 1 with a semi-rigid frame providing maximum comfort for a user and maximum stabilization by means of the medial shell section 13. Although not shown in the figures, it may be advantageously with respect to extending the lifespan of the ankle support 1 and/or obtaining an improved connection between elastic cover 7 and the lateral shell section 11 to stitch the elastic cover 7 to the stiffer zones 11*a*, 11*c* of the lateral shell section 11. The one-piece shell 9 is configured to leave the front part of the lower leg free such that the one-piece shell 9 provides a semi-rigid frame defining a user-friendly open instep space for receiving a foot and a lower leg of a user. Further, the sole shell section 17 comprises a reinforced sole zone 17 shown in FIG. 5 which extends between the medial shell section 13 and lateral shell section 11, wherein the reinforced sole zone 17*a* is stiffer than the lateral shell section 11 and/or the reinforced zone 15 of the medial shell section is stiffer than the reinforced sole zone 17*a*. The sole shell section 17 further comprises a further sole zone 17*b* which is more flexible than the reinforced sole zone 17*a*.

The medial shell section 13 and the lateral shell section 11 define a heel recess 55, in particular a heel recess 55 having an endless heel recess edge 51 in combination with the sole shell section 17. Above the heel recess 55 the medial shell section 13 and the lateral shell section 11 merge into another.

The ankle support 1 is made of materials such that the ankle support 1 can be machine-washed at 40 degrees Celsius.

The ankle support 1 can be worn on top of a sock and is configured to be worn in a normal shoe. The maximum thickness of the ankle support 1, normally the reinforced zone 15 of the medial shell section, is less than 5 mm, preferably less than 3 mm.

The invention claimed is:

1. An ankle support including a one-piece shell comprising:

a lateral shell section;

a medial shell section that is larger than the lateral shell section, the medial shell section including an elongated reinforced zone for providing support in the ankle support, wherein the lateral shell section is less stiff than the medial shell section;

a sole shell section connecting the lateral shell section and the medial shell section; and an elastic cover;

wherein:

the medial shell section includes a medial edge configured to extend upwards from the sole shell section along the medial side of lower leg and defining an open recess in the medial shell section for receiving the medial malleolus;

the lateral shell section includes a lateral edge configured to extend upwards from the sole shell section along the lateral side of the lower leg and defining an open recess in the lateral shell section for receiving the lateral malleolus;

the medial shell section extends farther upward from the sole shell section along the medial side of the lower leg than the lateral shell section extends from the sole shell section along the lateral side of the lower leg, the elongated reinforced zone extending along at least a portion of the upward extent of the medial shell section;

at least a portion of the lateral edge is connected to the elastic cover; and a portion of the elastic cover opposite the lateral edge is configured to be releasably connected to an upper portion of the medial shell section.

2. The ankle support according to claim 1, wherein at least a majority of a length of the lateral edge is connected to the elastic cover.

3. The ankle support according to claim 1, wherein the elastic cover comprises at least one strap section and a textile section, and wherein the textile section is more elastic than the at least one strap section.

4. The ankle support according to claim 3, wherein:

the at least one strap section comprises a first layer and a second layer arranged in a stacked configuration;

the first layer is less elastic than the textile section; and the second layer is formed by the textile section.

5. The ankle support according to claim 3, wherein the textile section comprises a double folded textile.

6. The ankle support according to claim 5, wherein an edge of the elastic cover, between the portion to be releasably connected to the upper portion of the medial shell section and the lateral edge, is provided by a fold line of the double folded textile of the textile section.

7. The ankle support according to claim 5, wherein an edge area of the elastic cover, extending between the sole section and the portion of the elastic cover to be releasably connected to the upper portion of the medial shell section, is provided by the at least one strap section.

8. The ankle support according to claim 7, wherein a further edge area of the elastic cover, connected to the lateral edge of the lateral shell section, is formed by the at least one strap section.

9. The ankle support according to claim 1, further comprising:

at least one strap including two strap portions, wherein each of the two strap portions is connected to the sole shell section; or two separate straps, wherein each strap is connected to the sole shell section;

wherein one of the two strap portions or one of the two straps is connected proximal to the sole shell section to the lateral shell section, and the other of the two strap portions or the other of the two straps is connected proximal to the sole shell section to the medial shell section.

10. The ankle support according to claim 9, further comprising at least one notch for guiding the at least one strap.

11. The ankle support according to claim 1, wherein circumferential edges of the one-piece shell are more flexible than the elongated reinforced zone of the medial shell section.

12. The ankle support according to claim 1, wherein the medial shell section and the lateral shell section together define a heel recess.

13. The ankle support according to claim 12, wherein the medial shell section and the lateral shell section merge into another at a position above the heel recess.

14. The ankle support according to claim 1, wherein in use, the one-piece shell is configured to leave a front part of a lower leg free such that the one-piece shell provides a semi-rigid frame defining an open instep space for receiving a foot and a lower leg of a user.

15. The ankle support according to claim 1, wherein the sole shell section comprises a reinforced sole zone that extends between the medial and lateral shell sections, and wherein the reinforced sole zone is stiffer than the lateral shell section.

16. The ankle support according to claim 15, wherein the elongated reinforced zone of the medial shell section is stiffer than the reinforced sole zone.

17. The ankle support according to claim 1, wherein the elongated reinforced zone of the medial shell section extends from or proximal to the sole shell section along the medial malleolus further upwards.

18. The ankle support according to claim 1, wherein the one-piece shell is made by multi-material injection molding.

19. The ankle support according to claim 1, wherein the lateral shell section comprises at least one zone that is stiffer than another zone of the lateral shell section and is less stiff than the elongated reinforced zone of the medial shell section.

* * * * *